United States Patent
Sheng et al.

(10) Patent No.: US 10,316,003 B2
(45) Date of Patent: Jun. 11, 2019

(54) METHOD OF SYNTHESIZING PROTHIOCONAZOLE AND OPTICALLY ACTIVE ISOMERS THEREOF AND INTERMEDIATES

(71) Applicant: ORIENTAL (LUZHOU) AGROCHEMICALS. CO., LTD., Luzhou, Sichuan (CN)

(72) Inventors: Qiuju Sheng, Zhejiang (CN); Zhiming Zhang, Zhejiang (CN); Junliang Wang, Zhejiang (CN); Bangchi Chen, Zhejiang (CN)

(73) Assignee: ORIENTAL (LUZHOU) AGROCHEMICALS. CO., LTD., Sichuan (CN)

( * ) Notice: Subject to any disclaimer, the term of this patent is extended or adjusted under 35 U.S.C. 154(b) by 0 days.

(21) Appl. No.: 16/236,039

(22) Filed: Dec. 28, 2018

(65) Prior Publication Data

US 2019/0135766 A1    May 9, 2019

Related U.S. Application Data

(63) Continuation of application No. PCT/CN2017/089955, filed on Jun. 26, 2017.

(51) Int. Cl.
*C07D 249/12* (2006.01)
*C07C 251/78* (2006.01)

(52) U.S. Cl.
CPC .......... *C07D 249/12* (2013.01); *C07C 251/78* (2013.01); *C07B 2200/07* (2013.01)

(58) Field of Classification Search
CPC .................. C07D 249/12; C07B 2200/07; C07C 251/78
USPC ....................................... 548/263.2
See application file for complete search history.

(56) References Cited

U.S. PATENT DOCUMENTS 4,913,727 A    4/1990    Stroech et al.

FOREIGN PATENT DOCUMENTS

| CN | 1274346 A | 11/2000 |
| CN | 1274347 A | 11/2000 |
| CN | 1274348 A | 11/2000 |
| CN | 1411450 A | 4/2003 |
| CN | 105949137 A | 9/2016 |

OTHER PUBLICATIONS

Joachim G. Schantl, et al. Oxidation and rearrangement of 5-substituted 5-ethoxycarbonyl [1,2,4] triazolidine-3-thiones, Heterocycles, 1999, 50(1): 251-258.
Tang Liping, et al. Synthesis Process of Intermediate of Prothiconazole, Chemical Industry and Engineering Progress, 2015, 34(7):1989-1992.

*Primary Examiner* — Kristin A Vajda
(74) *Attorney, Agent, or Firm* — Wayne & Ken, LLC; Tony Hom

(57) ABSTRACT

Disclosed are a method of synthesizing prothioconazole and optically active isomers thereof and intermediates. The method includes reacting hydrazine with glyoxylic acid to produce a hydrazono acetic acid as an intermediate, and then reacting the intermediate with thiocyanate to produce the target product prothioconazole. The present method is very specific in terms of regioselectivity, resulting in minimum byproducts and a high product yield. The present method does not require special equipment, nor anhydrous or oxygen-free manipulations. The process is simple and generates minimum wastes, suitable for industrial production.

13 Claims, No Drawings

METHOD OF SYNTHESIZING PROTHIOCONAZOLE AND OPTICALLY ACTIVE ISOMERS THEREOF AND INTERMEDIATES

CROSS-REFERENCE TO RELATED APPLICATIONS

This application is a continuation of International Patent Application No. PCT/CN2017/089955, filed on Jun. 26, 2017, which claims the benefit of priority from Chinese Application No. 201610561636.2, filed on Jul. 15, 2016. The contents of the aforementioned applications, including any intervening amendments thereto, are incorporated herein by reference in its entirety.

TECHNICAL FIELD

The present disclosure relates to organic synthesis, and more specifically to a method of synthesizing prothioconazole and optically active isomers thereof and intermediates.

BACKGROUND

Prothioconazole, developed by Bayer Corporation, is a novel thio-triazole fungicide (U.S. Pat. No. 5,789,430A). The prothioconazole compound has a structure of formula 1

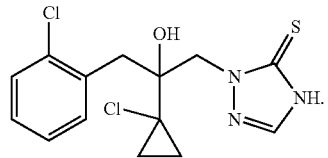

Prothioconazole is a class of demethylation inhibitors (DMIs), which acts through inhibiting 14-demethylation of lanosterol as a precursor of sterol in fungi. Prothioconazole has not only good systemic action and excellent protection, treatment and eradication activities, but also durable efficacy. A variety of field efficacy trials have demonstrated that prothioconazole has good safety profile to crops and favorable effects on disease prevention and cure as well as significant increase in yield. Moreover, prothioconazole provides broader-spectrum fungicidal activities compared to triazoles as fungicides.

Currently, prothioconazole is mainly used for preventing and curing numerous diseases of cereal crops such as wheat, barley, oilseed rape, peanuts, rice, legume crops, etc. Prothioconazole shows excellent prevention and cure effects on almost all diseases of wheat and barley, for example powdery mildew, banded sclerotial blight, fusarium wilt, leaf spot, rust, stalk break, net blotch and *Rhynchosporium secalis*. Prothioconazole can also prevent and cure soil-borne diseases such as sclerotium diseases and folia diseases such as gray mold, black spot, brown patch, black shank and rust on oilseed rape and peanuts.

U.S. Pat. No. 8,188,129B2 discloses an optically active isomer of prothioconazole.

Strategy of producing prothioconazole can be classified into two categories according to the origin of the sulfur atom. The first strategy of producing prothioconazole is through reaction of hyroxytriazole compound 2 as a key intermediate with sulfur (U.S. Pat. No. 4,913,727). Sulfur is the thio source for prothioconazole in such reaction. In this method, a substitution reaction of a chloride 3 (U.S. Pat. No. 4,913,727) or an epoxide 4 (U.S. Pat. No. 5,146,001) as a starting material with a triazole 5 may give the key intermediate 2. This substitution reaction also produces a significant amount of regioisomer 6 which needs to be removed by purification, thereby resulting in a lower yield (51-53%). The key intermediate 2 may be prepared through a reaction of a chloroketone 7 as a raw material and triazole 5 followed by a reaction with Grignard reagent 10, however, this method suffers similarly from regioselectivity.

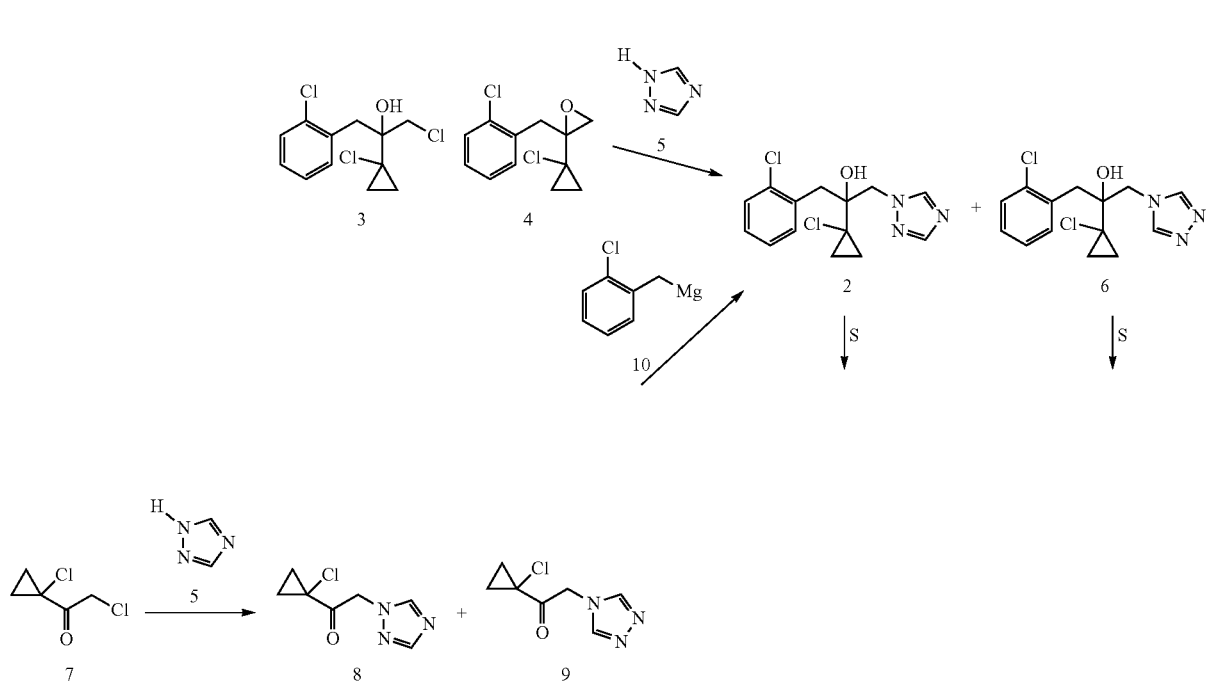

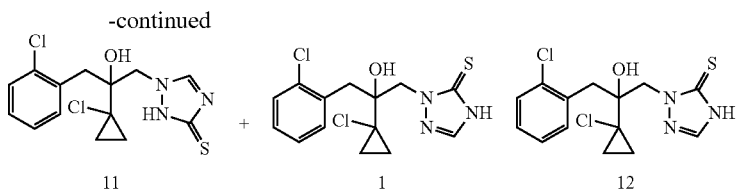

U.S. Pat. No. 5,789,430 discloses a method of preparing prothioconazole through a direct reaction of a compound 2 and sulfur. Such reaction is carried out in the presence of N-methyl pyrrolidone as a solvent at 200° C. for 44 hours to produce prothioconazole (20% yield). In U.S. Pat. No. 6,172,236, a higher yield (75%) is obtained through the reaction in DMF at 140-160° C. where air is introduced, however, the reaction yield is still not satisfactory.

U.S. Pat. No. 5,789,430 also discloses an improved method of producing prothioconazole through a reaction of compound 2 and sulfur. In this method, deprotonation of compound 2 in THF solvent using n-BuLi is carried out followed by a reaction with sulfur. As a result, the yield of prothioconazole is greatly increased (93% yield). However, such process requires anhydrous, oxygen-free and ultra-low temperature conditions and the related equipment, and requires more than two equivalents of highly hazardous n-BuLi reagent. Therefore, it is not suitable for industrial production due to high cost and safety concerns. In addition, chemical regioselectivity also becomes problematic in this process. For example, (1) lack of control in the deprotonation of key intermediate 2 using n-BuLi will lead to formation of regioisomeric impurity 11; and (2) if the regioisomer 6 is not completely separated and removed during the production of key intermediate 2, it will result in a regioisomer impurity 12. These highly challenging separation and purification not only produce a large amount of wastes, but also greatly increase the cost at the same time.

US2013005985 discloses a method of preparing prothioconazole through deprotonation of compound 2 using Grignard reagent such as i-PrMgCl instead of n-BuLi followed by sulfurization. This method solves the safety problem associated with using n-BuLi reagent. Such process, however, still requires anhydrous, oxygen-free and ultra-low temperature conditions and the related equipment, and requires more than two equivalents of Grignard reagent. In addition, the yield is greatly reduced (from 93% of using n-BuLi to 68%).

DE4030039 discloses another method of preparing intermediate 2. This method employs epoxide 4 as a starting material to produce the target compound 2 through hydrazinolysis followed by a reaction with formamidine acetate. Such method successfully solves the regioselectivity problem in the above preparation of compound 2 through substitution with triazole 5, but the total yield is not desirable (64%).

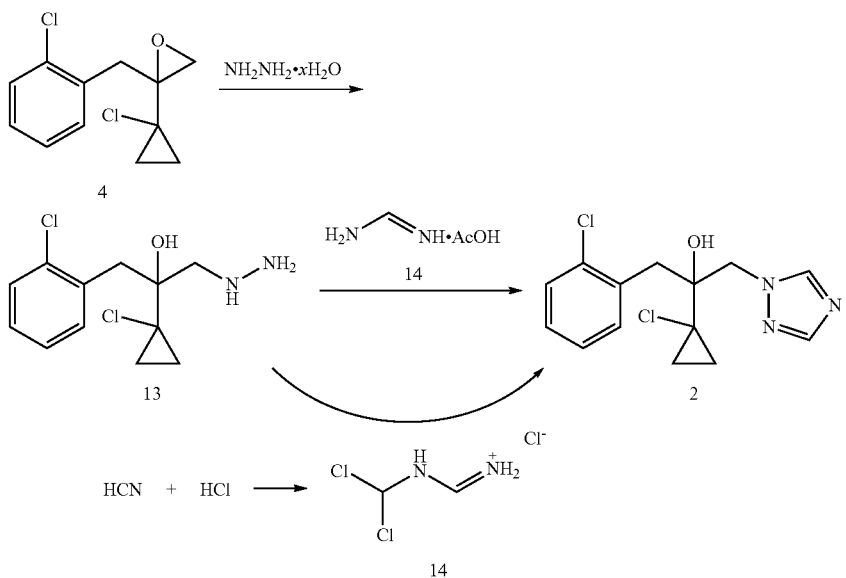

U.S. Pat. No. 6,720,428 discloses a method of preparing intermediate 2 through a reaction of a compound 13 and N-dichloromethylformamidine chloride 14. This method has a very good triazole cyclization yield (99.6%), but N-dichloromethylformamidine chloride 14 needs to be prepared starting from the highly toxic HCN.

The second strategy of producing prothioconazole is through the use of thiocyanate as a sulfur atom contributor for prothioconazole molecule. U.S. Pat. No. 6,262,276 discloses a method where a thiosemicarbazide intermediate 16 is synthesized through a reaction of hydroxyhydrazine 15 and a thiocyanate such as ammonium thiocyanate and then the intermediate 16 is used to produce prothioconazole. This method solves to a great extent the problems associated with the first strategy of preparing prothioconazole, but this method still suffers from the problem of its own chemical regioselectivity during the production of thiosemicarbazide intermediate 16 (the purity of the product 16 is only 65.9%). Regioisomeric impurity 17 needs to be strictly controlled, otherwise in the next step reaction formation of isomeric impurity 11 will result.

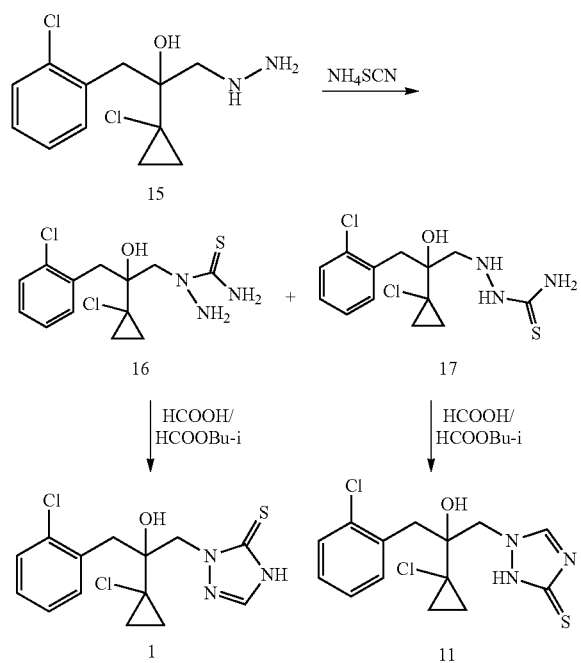

U.S. Pat. No. 6,271,389 discloses a method of preparing prothioconazole through a reaction of hydroxyhydrazine 15 and a thiocyanate such as potassium thiocyanate in the presence of alkyl (aryl) aldehyde or ketone to produce intermediate 18 followed by a reaction with HCOOH/HCOOBu-i. As compared to the method disclosed in U.S. Pat. No. 6,262,276, the yield during production of intermediate 18 (U.S. Pat. No. 6,271,389) is increased to some degree (82%), but a deprotection is required in the next step, resulting in a yield decrease of greater than 10%. In addition, this method cannot eliminate the problem of formation of the regioisomeric impurity 19 completely.

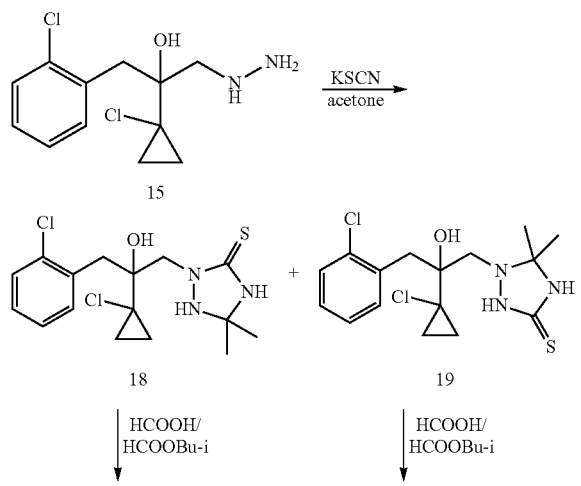

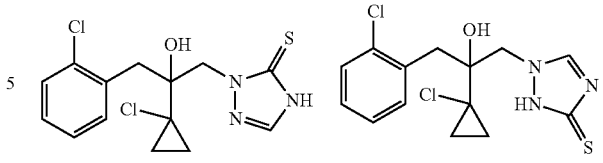

U.S. Pat. No. 6,201,128 discloses another method of synthesizing prothioconazole using hydroxyhydrazine 15 as a starting material. Such method employs formaldehyde instead of alkyl (aryl) aldehyde or ketone (U.S. Pat. No. 6,271,389) to prepare an intermediate 20 followed by an oxidative dehydrogenation of intermediate 20 to produce prothioconazole. This method has an advantage of atom efficiency in the last step of reaction as compared to the method described in U.S. Pat. No. 6,271,389. The alkyl (aryl) aldehyde or ketone in U.S. Pat. No. 6,271,389 only acts as a protecting group, while the formaldehyde in U.S. Pat. No. 6,201,128 becomes part of the molecule of prothioconazole. However, compared to the intermediate 18 in U.S. Pat. No. 627,189, the intermediate 20 in U.S. Pat. No. 6,201,128 is relatively unstable due to less steric-hindrance because of the lack of two methyl groups. Additionally, since the formaldehyde is more active than acetone, the active protons in intermediate 20 tend to react readily with the formaldehyde to give polymeric byproducts. Moreover, this method does not completely eliminate the problem of formation of the regioisomeric impurity 21.

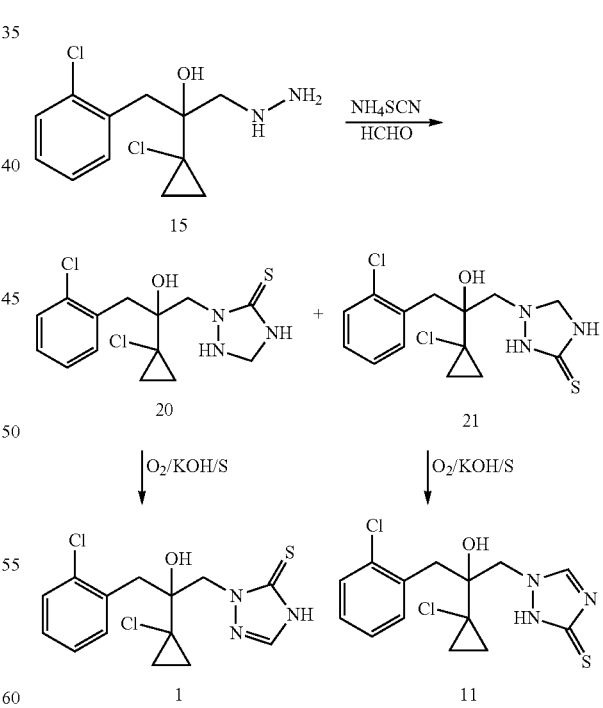

U.S. Pat. No. 6,559,317 discloses a method of preparing prothioconazole via FeCl$_3$ mediated intermediate 20. Although the yield of the oxidation reaction is improved to some degree, the treatment of iron-containing wastes is an environmental problem.

SUMMARY

The present application provides a method of synthesizing prothioconazole and optically active isomers thereof, and intermediates in order to solve the problems in the prior art.

The method of synthesizing prothioconazole and optically active isomers thereof includes the following steps:

step 1: reacting compound 22 or compound 22' with compound 23 or compound 23' according to the following scheme to produce compound 24 or compound 24':

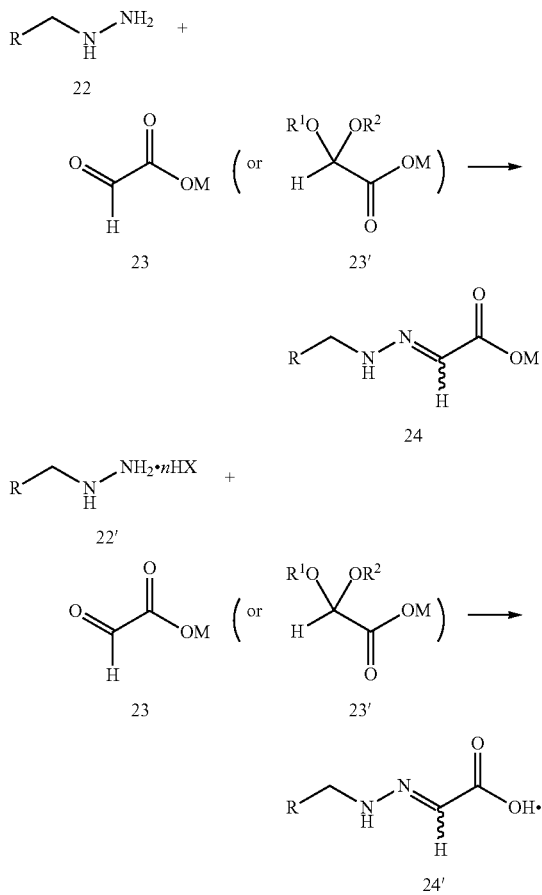

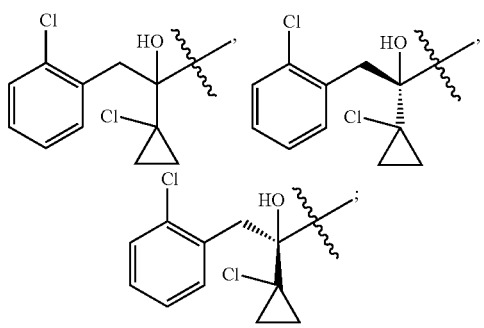

wherein:
R is selected from step 2: reacting compound 24 or compound 24' with thiocyanate (M'SCN) to produce the prothioconazole compound 1 or optically active isomers thereof, as shown in the following reaction scheme:

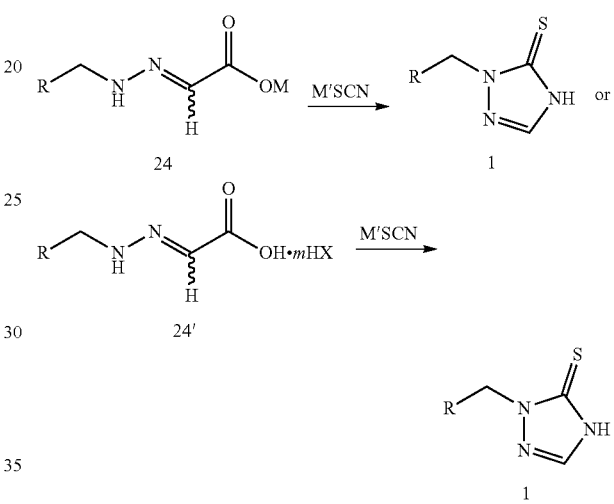

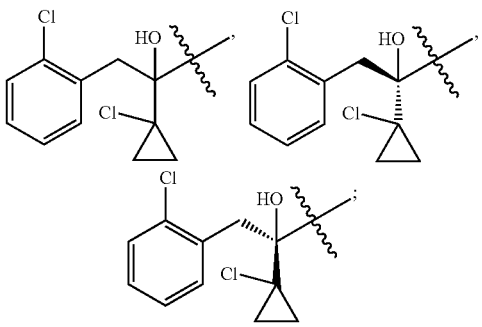

wherein:
R is selected from $R^1$ and $R^2$ are independently hydrogen or a $C_1$-$C_6$ alkyl group; or $R^1$, $R^2$ taking together forms a ring selected from dimethylene, trimethylene, tetramethylene, or pentamethylene group;

n is 0.5, 1 or 2;

HX is selected from a haloid acid, a sulfuric acid or a phosphoric acid;

M is selected from hydrogen, an alkali metal or a $NR^3R^4R^5R^6$ group where $R^3$, $R^4$, $R^5$ and $R^6$ are independently hydrogen, a $C_1$-$C_{18}$ alkyl group or a $C_6$-$C_{18}$ aryl group;

m is 0 or 1; and

M is selected from hydrogen, an alkali metal or a $NR^3R^4R^5R^6$ group where $R^3$, $R^4$, $R^5$ and $R^6$ are independently hydrogen, a $C_1$-$C_{18}$ alkyl group or a $C_6$-$C_{18}$ aryl group;

M' is selected from an alkali metal or a $NR^3R^4R^5R^6$ group where $R^3$, $R^4$, $R^5$ and $R^6$ are independently hydrogen, a $C_1$-$C_{18}$ alkyl group or $C_6$-$C_{18}$ aryl group;

m is 0 or 1; and

HX is selected from a haloid acid, a sulfuric acid or a phosphoric acid.

Specifically, step 1 may be carried out in the absence or presence of a solvent. The solvent is preferably selected from water, acetonitrile, tert-butanol, dichloromethane, DMF, DMSO and methylbenzene or mixture thereof. A molar ratio of compound 22 or compound 22' to compound 23 (or compound 23') is preferably 1:1-10. A reaction temperature in step 1 is preferably 0-40° C. Preferably, step 2 is carried out in the presence of an acid. The acid may act as a catalyst or directly a solvent. Preferably, the acid is an organic acid selected from a formic acid, an acetic acid, a trifluoroacetic acid, a methanesulfonic acid and a p-toluenesulfonic acid or mixture thereof. A molar ratio of the acid to compound 24 or compound 24' is preferably 0.01-100:1. A molar ratio of compound 24 or compound 24' to the thiocyanate is preferably 1:1-5. A reaction temperature in step 2 is preferably 50-80° C.

Steps 1 and 2 may be carried out in a stepwise or a one-spot manner.

A method of synthesizing prothioconazole or optically active isomers thereof includes the following step:

reacting compound 24 or compound 24' with thiocyanate (M'SCN) to produce the prothioconazole compound 1 or optically active isomers thereof, as shown in the following reaction scheme:

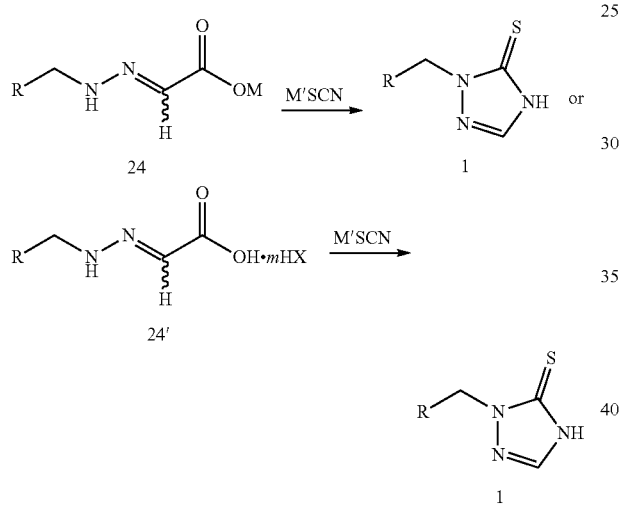

wherein:
R is selected from

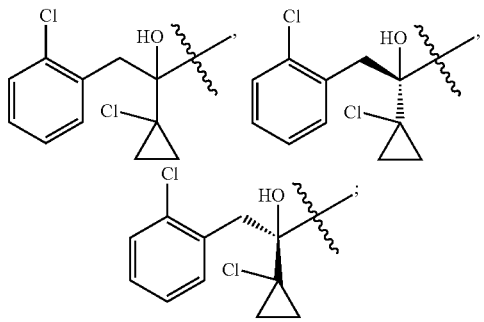

M is selected from hydrogen, an alkali metal or a NR³R⁴R⁵R⁶ group where R³, R⁴, R⁵ and R⁶ are independently hydrogen, a $C_1$-$C_{18}$ alkyl group or a $C_6$-$C_{18}$ aryl group;

M' is selected from an alkali metal or a NR³R⁴R⁵R⁶ group where R³, R⁴, R⁵ and R⁶ are independently hydrogen, a $C_1$-$C_{18}$ alkyl group or a $C_6$-$C_{18}$ aryl group;

m is 0 or 1; and

HX is selected from a haloid acid, a sulfuric acid or a phosphoric acid.

Specifically, the reaction is preferably carried out in the presence of an acid. The acid may act as a catalyst or directly as a solvent. Preferably, the acid is an organic acid selected from a formic acid, an acetic acid, a trifluoroacetic acid, a methanesulfonic acid and a p-toluenesulfonic acid or mixture thereof. A molar ratio of the acid to compound 24 or compound 24' is preferably 0.01-100:1. A molar ratio of compound 24 or compound 24' to the thiocyanate is preferably 1:1-5. A reaction temperature is preferably 50-80° C.

The present application provides a compound 24 shown as the following formula:

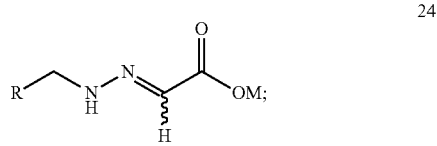

wherein:
R is selected from

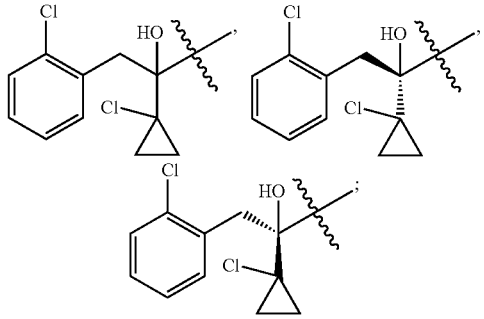

and

M is selected from hydrogen, an alkali metal or a NR³R⁴R⁵R⁶ group where R³, R⁴, R⁵ and R⁶ are independently hydrogen, a $C_1$-$C_{18}$ alkyl group or a $C_6$-$C_{18}$ aryl group. The present application further provides a compound 24' shown as the following formula:

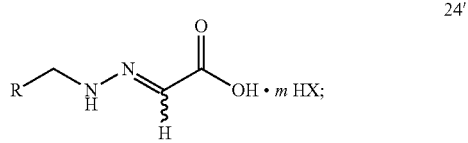

wherein:
R is selected from

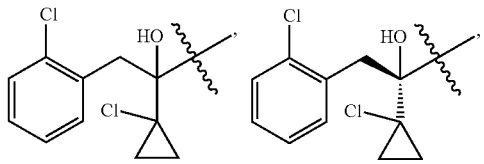

-continued

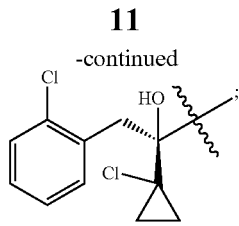

m is 0 or 1; and
HX is selected from a haloid acid, a sulfuric acid or a phosphoric acid.

The method of synthesizing prothioconazole and optically active isomers thereof and intermediates has the following advantages:

(1) The present method is very specific in terms of regioselectivity, resulting in minimum byproducts and high product yield.

(2) The present method does not require special equipment, nor anhydrous or oxygen-free manipulations.

(3) The process is simple and generates minimum wastes, suitable for industrial production.

DETAILED DESCRIPTION OF EMBODIMENTS

The following embodiments are intended to illustrate the features of the present invention. The scope of the application is not limited to these embodiments.

Example 1: synthesis of 2-{2-[2-(1-chlorocyclopropyl)-3-(2-chlorophenyl)-2-hydroxypropyl]hydrazono}acetic acid To a 250 mL reaction flask were added 15.5 g of 2-(1-chlorocyclopropyl)-1-(2-chlorophenyl)-3-hydrazinopropan-2-ol hydrochloride, 120 mL of water and 15 mL of acetonitrile. Then 7.5 g of 50% glyoxylic acid solution was added dropwise. The reaction mixture was stirred at room temperature. After the reaction was complete, the reaction mixture was filtered, washed with water and dried to give 16.4 g of product as a solid (99% yield).
$^1$H NMR (δ, CDCl$_3$): 7.456-7.437 (m, 1H), 7.405-7.386 (m, 1H), 7.271-7.252 (m, 1H), 7.245-7.223 (m, 1H), 6.971-6.899 (t, 1H), 6.781 (s, 1H), 3.906-3.898, 3.878-3.869 (dd, 1H), 3.547-3.519 (d, 1H), 3.519-3.508, 3.491-3.480 (dd, 1H), 3.211-3.183 (d, 1H), 2.506 (s, 2H), 1.175-1.134 (m, 1H), 0.964-0.852 (m, 3H); MS: m/z=330.9 ([M+1]$^+$).

Example 2: synthesis of (2R)-2-{2-[2-(1-chlorocyclopropyl)-3-(2-chlorophenyl)-2-hydroxypropyl]hydrazono}acetic acid To a 250 mL reaction flask were added 13.7 g of (2R)-2-(1-chlorocyclopropyl)-1-(2-chlorophenyl)-3-hydrazinopropan-2-ol, 100 mL of water and 20 mL of acetonitrile. Then 7.5 g of 50% glyoxylic acid solution was added dropwise. The reaction mixture was stirred at room temperature. After the reaction was complete, the reaction mixture was filtered, washed with water and dried to give 15.2 g of product as a solid (92% yield).

Example 3: synthesis of (2S)-2-{2-[2-(1-chlorocyclopropyl)-3-(2-chlorophenyl)-2-hydroxypropyl]hydrazono}acetic acid To a 250 mL reaction flask were added 13.7 g of (2S)-2-(1-chlorocyclopropyl)-1-(2-chlorophenyl)-3-hydrazinopropan-2-ol, 100 mL of water and 20 mL of acetonitrile. Then 7.5 g of 50% glyoxylic acid solution was added dropwise. The reaction mixture was stirred at room temperature. After the reaction was complete, the reaction mixture was filtered, washed with water and dried to give 15.0 g of product as a solid (91% yield).

Example 4: synthesis of 2-{2-[2-(1-chlorocyclopropyl)-3-(2-chlorophenyl)-2-hydroxypropyl]hydrazono}acetic acid To a 250 mL reaction flask was added 15.5 g of 2-(1-chlorocyclopropyl)-1-(2-chlorophenyl)-3-hydrazinopropan-2-ol hydrochloride. 7.5 g of 50% glyoxylic acid solution was added dropwise. The reaction mixture was stirred at room temperature. After the reaction was complete, the reaction mixture was filtered, washed with water and dried to give 16.0 g of product as a solid (97% yield).

Example 5: synthesis of 2-{2-[2-(1-chlorocyclopropyl)-3-(2-chlorophenyl)-2-hydroxypropyl]hydrazono}acetic acid To a 250 mL reaction flask were added 15.5 g of 2-(1-chlorocyclopropyl)-1-(2-chlorophenyl)-3-hydrazinopropan-2-ol hydrochloride and 100 mL of water. 10 g of 50% glyoxylic acid solution was added dropwise. The reaction mixture was stirred at room temperature. After the reaction was complete, the reaction mixture was filtered, washed with water and dried to give 15.7 g of product as a solid (95% yield).

Example 6: synthesis of 2-{2-[2-(1-chlorocyclopropyl)-3-(2-chlorophenyl)-2-hydroxypropyl]hydrazono}acetic acid To a 250 mL reaction flask were added 13.7 g of 2-(1-chlorocyclopropyl)-1-(2-chlorophenyl)-3-hydrazinopropan-2-ol and 150 mL of dichloromethane. 9.6 g of 50% glyoxylic acid solution was added dropwise. The reaction mixture was stirred at room temperature. After the reaction was complete, the solvent was removed to give 15.4 g of product as a solid (93% yield).

Example 7: synthesis of 2-{2-[2-(1-chlorocyclopropyl)-3-(2-chlorophenyl)-2-hydroxypropyl]hydrazono}acetic acid To a 250 mL reaction flask were added 13.7 g of 2-(1-chlorocyclopropyl)-1-(2-chlorophenyl)-3-hydrazinopropan-2-ol and 100 mL of water. 4.7 g of glyoxylic acid monohydrate was added in portions. The reaction mixture was stirred at room temperature. After the reaction was complete, the reaction mixture was filtered, washed with water and dried to give 14.5 g of product as a solid (88% yield).

Example 8: synthesis of sodium 2-{2-[2-(1-chlorocyclopropyl)-3-(2-chlorophenyl)-2-hydroxypropyl]hydrazono}acetate To a 250 mL reaction flask were added 13.7 g of 2-(1-chlorocyclopropyl)-1-(2-chlorophenyl)-3-hydrazinopropan-2-ol and 150 mL of dichloromethane. 12.5 g of 50% sodium glyoxylate solution was added dropwise. The reaction mixture was stirred at room temperature. After the reaction was complete, the solvent was removed. 14.9 g of a solid product was obtained by lyophilization (90% yield).

Example 9: synthesis of sodium 2-{2-[2-(1-chlorocyclopropyl)-3-(2-chlorophenyl)-2-hydroxypropyl]hydrazono}acetate To a 250 mL reaction flask were added 16.5 g of 2-{2-[2-(1-chlorocyclopropyl)-3-(2-chlorophenyl)-2-hydroxypropyl]hydrazono}acetic acid and 150 mL of ethanol. 4 g of 50% sodium hydroxide aqueous solution was added dropwise. The reaction was stirred at room temperature. After the reaction was complete, the solvent was removed. 17.4 g of a solid product was obtained by lyophilization (99% yield).

Example 10: synthesis of 2-{2-[2-(1-chlorocyclopropyl)-3-(2-chlorophenyl)-2-hydroxypropyl]hydrazono}acetic acid hemisulfate To a 25 mL reaction flask were added 1.37 g of 2-(1-chlorocyclopropyl)-1-(2-chlorophenyl)-3-hydrazinopropan-2-ol and 15 mL of acetonitrile. 0.96 g of 50% glyoxylic acid solution and 0.25 g of concentrated sulfuric acid were added dropwise. The reaction mixture was stirred at room temperature. After the reaction was complete, the solvent was removed. 1.89 g of a solid product was obtained by lyophilization (99% yield).

Example 11: synthesis of 2-{2-[2-(1-chlorocyclopropyl)-3-(2-chlorophenyl)-2-hydroxypropyl]hydrazono}acetic acid hemisulphate To a 250 mL reaction flask were added 3.3 g of 2-{2-[2-(1-chlorocyclopropyl)-3-(2-chlorophenyl)-2-hydroxypropyl]hydrazono}acetic acid and 10 mL of acetonitrile. 0.5 g of concentrated sulfuric acid was added dropwise. The reaction mixture was stirred at room temperature. After the reaction was complete, the solvent was removed. 3.8 g of a solid product was obtained by lyophilization (99% yield).

Example 12: synthesis of 2-[2-(1-chlorocyclopropyl)-3-(2-chlorophenyl)-2-hydroxypropyl]-1,2,4-triazo-3-thione To a 250 mL reaction flask were added 16.5 g of 2-{2-[2-(1-chlorocyclopropyl)-3-(2-chlorophenyl)-2-hydroxypropyl]hydrazono}acetic acid, 6.1 g of sodium thiocyanate and 80 mL of acetic acid. The reaction was heated to 80° C. After the reaction was complete, the reaction mixture was concentrated. 16.3 g of a solid product was obtained by adding with toluene, washing with water and distillation (95% yield).

$^1$H NMR (δ, CDCl$_3$): 12.300 (s, 1H), 7.856 (s, 1H), 7.549-7.544, 7.534-7.530 (dd, 1H), 7.377-7.374, 7.362-7.358 (dd, 1H), 7.242-7.183 (m, 2H), 4.802-4.773 (d, 1H), 4.510-4.481 (d, 1H), 4.212 (s, 1H), 3.621-3.594 (d, 1H), 3.193-3.166 (d, 1H), 0.943-0.922 (m, 1H), 0.885-0.767 (m, 3H); MS: m/z=343.9 ([M+1]$^+$).

Example 13: synthesis of 2-[2-(1-chlorocyclopropyl)-3-(2-chlorophenyl)-2-hydroxypropyl]-1,2,4-triazo-3-thione To a 25 mL reaction flask were added 1.89 g of 2-{2-[2-(1-chlorocyclopropyl)-3-(2-chlorophenyl)-2-hydroxypropyl]hydrazono}acetic acid hemisulphate, 0.62 g of sodium thiocyanate and 10 mL of acetic acid. The reaction was heated to 50° C. After the reaction was complete, the reaction mixture was concentrated. 1.43 g of a solid product was obtained by adding with toluene, washing with water and distillation (83% yield).

Example 14: synthesis of 2-[2-(1-chlorocyclopropyl)-3-(2-chlorophenyl)-2-hydroxypropyl]-1,2,4-triazo-3-thione To a 250 mL reaction flask were added 17.6 g of sodium 2-{2-[2-(1-chlorocyclopropyl)-3-(2-chlorophenyl)-2-hydroxypropyl]hydrazono}acetate, 6.1 g of sodium thiocyanate and 25 mL of acetic acid. The reaction was heated to 80° C. After the reaction was complete, the reaction mixture was concentrated. 14.6 g of a solid product was obtained by adding with toluene, washing with water and distillation (85% yield).

Example 15: synthesis of 2-[2-(1-chlorocyclopropyl)-3-(2-chlorophenyl)-2-hydroxypropyl]-1,2,4-triazo-3-thione To a 250 mL reaction flask were added 16.5 g of 2-{2-[2-(1-chlorocyclopropyl)-3-(2-chlorophenyl)-2-hydroxypropyl]hydrazono}acetic acid, 3.8 g of ammonium thiocyanate and 25 mL of formic acid. The reaction was heated to 50° C. After the reaction was complete, the reaction mixture was concentrated. 13.8 g of a solid product was obtained by adding with toluene, washing with water and distillation (80% yield).

Example 16: synthesis of (R)-2-{2-[2-(1-chlorocyclopropyl)-3-(2-chlorophenyl)-2-hydroxypropyl]-1,2,4-triazo-3-thione To a 250 mL reaction flask were added 16.5 g of (2R)-2-{2-[2-(1-chlorocyclopropyl)-3-(2-chlorophenyl)-2-hydroxypropyl]hydrazono}acetic acid, 24.3 g of potassium thiocyanate and 25 mL of trifluoroacetic acid. The reaction was heated to 80° C. After the reaction was complete, the reaction mixture was concentrated. 15.5 g of a solid product was obtained by adding with toluene, washing with water and distillation (90% yield).

Example 17: synthesis of (S)-2-[2-(1-chlorocyclopropyl)-3-(2-chlorophenyl)-2-hydroxypropyl]-1,2,4-triazo-3-thione To a 250 mL reaction flask were added 16.5 g of (2S)-2-{2-[2-(1-chlorocyclopropyl)-3-(2-chlorophenyl)-2-hydroxypropyl]hydrazono}acetic acid, 24.3 g of potassium thiocyanate and 25 mL of trifluoroacetic acid. The reaction was heated to 80° C. After the reaction was complete, the reaction mixture was concentrated. 15.2 g of a solid product was obtained by adding with toluene, washing with water and distillation (88% yield).

Example 18: synthesis of 2-[2-(1-chlorocyclopropyl)-3-(2-chlorophenyl)-2-hydroxypropyl]-1,2,4-triazo-3-thione To a 100 mL reaction flask were added 0.93 g of 2-(1-chlorocyclopropyl)-1-(2-chlorophenyl)-3-hydrazinopropan-2-ol hydrochloride, 15 mL of acetonitrile, 0.55 g of a 50% glyoxylic acid solution and 0.24 g of sodium thiocyanate. The reaction was heated to 60° C. After the reaction was complete, 10 mL of water was added, the pH of the reaction mixture was adjusted to 2. The phases were separated, the aqueous phase was extracted using toluene, the organic phases were combined and concentrated to give 0.92 g of product as a solid (89% yield).

What is claimed is:

1. A method of synthesizing prothioconazole or optically active isomers thereof, comprising:

step 1: reacting compound 22 or compound 22' with compound 23 or compound 23' to produce compound 24 or compound 24', as shown in the following reaction scheme:

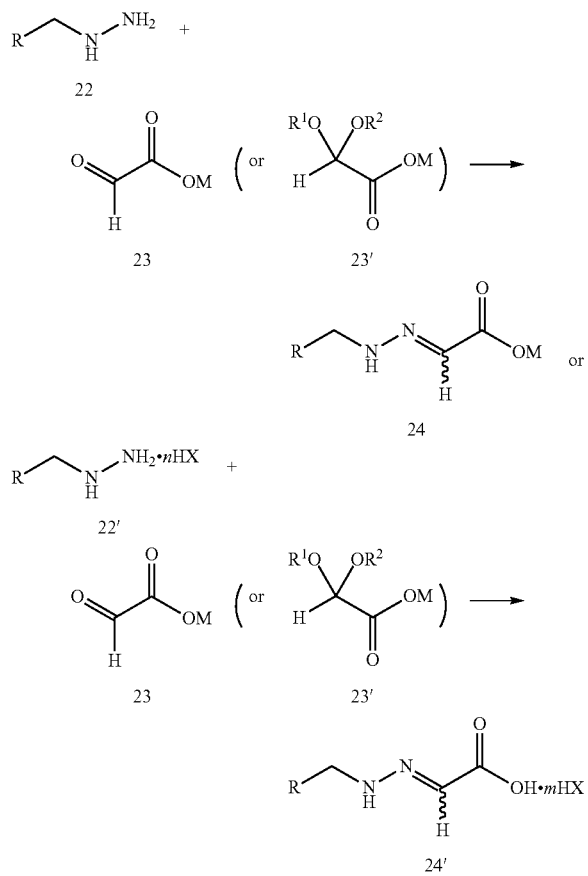

wherein:
R is selected from

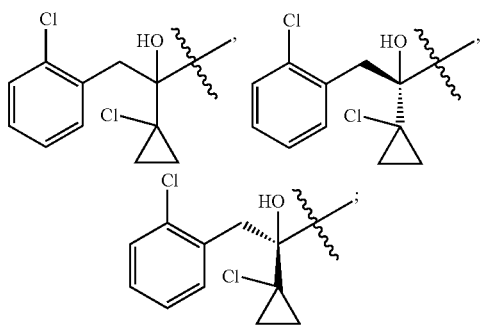

$R^1$ and $R^2$ are independently hydrogen or a $C_1$-$C_6$ alkyl group; or $R^1$, $R^2$ taking together to form a ring selected from dimethylene, trimethylene, tetramethylene, or pentamethylene group;

n is 0.5, 1 or 2;

HX is selected from a haloid acid, a sulfuric acid or a phosphoric acid;

M is selected from hydrogen, an alkali metal or a $NR^3R^4R^5R^6$ group where $R^3$, $R^4$, $R^5$ and $R^6$ are independently hydrogen, a $C_1$-$C_{18}$ alkyl group or a $C_6$-$C_{18}$ aryl group; and m is 0 or 1; and step 2: reacting compound 24 or compound 24' with thiocyanate (M'SCN) to produce the prothioconazole compound 1 or optically active isomers thereof, as shown in the following reaction scheme:

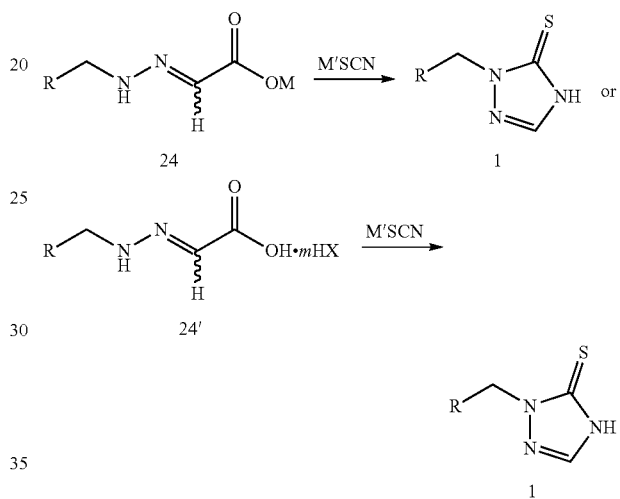

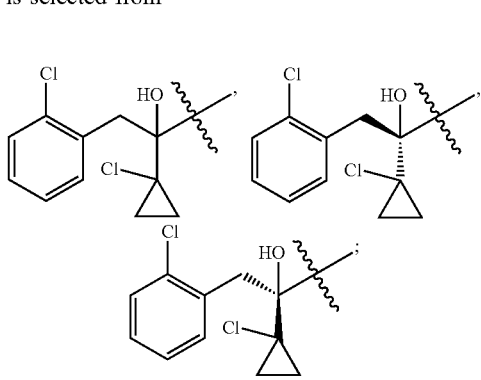

wherein:
R is selected from

M is selected from hydrogen, an alkali metal or a $NR^3R^4R^5R^6$ group where $R^3$, $R^4$, $R^5$ and $R^6$ are independently hydrogen, a $C_1$-$C_{18}$ alkyl group or a $C_6$-$C_{18}$ aryl group;

M' is selected from an alkali metal or a $NR^3R^4R^5R^6$ group where $R^3$, $R^4$, $R^5$ and $R^6$ are independently hydrogen, a $C_1$-$C_{18}$ alkyl group or $C_6$-$C_{18}$ aryl group;

m is 0 or 1; and

HX is selected from a haloid acid, a sulfuric acid or a phosphoric acid.

2. The method of claim 1, wherein step 1 is carried out in the presence or absence of a solvent; a molar ratio of compound 22 or compound 22' to compound 23 or compound 23' is 1:1-10; and a reaction temperature in step 1 is 0-40° C.

3. The method of claim 2, wherein the solvent is selected from water, acetonitrile, tert-butanol, dichloromethane, DMF, DMSO and methylbenzene or mixture thereof.

4. The method of claim 1, wherein steps 1 and 2 are carried out in a stepwise or a one-spot manner.

5. A method of synthesizing prothioconazole or optically active isomers thereof, comprising:

reacting compound 24 or compound 24' with thiocyanate (M'SCN) to produce the prothioconazole compound 1 or optically active isomers thereof, as shown in the following reaction scheme:

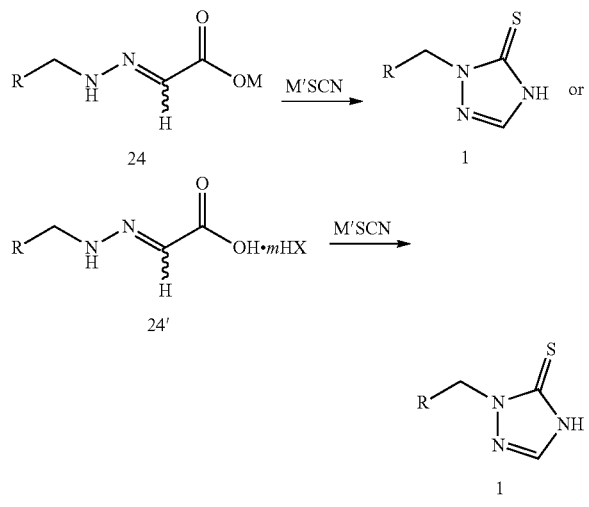

wherein:
R is selected from

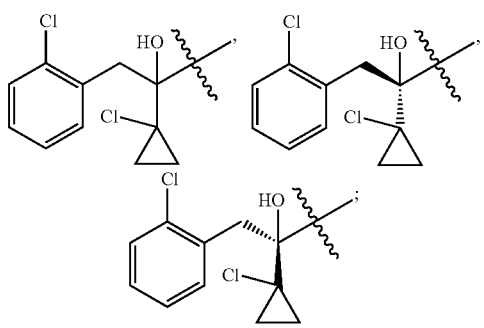

M is selected from hydrogen, an alkali metal or a NR³R⁴R⁵R⁶ group where $R^3$, $R^4$, $R^5$ and $R^6$ are independently hydrogen, a $C_1$-$C_{18}$ alkyl group or a $C_6$-$C_{18}$ aryl group;

M' is selected from an alkali metal or a NR³R⁴R⁵R⁶ group where $R^3$, $R^4$, $R^5$ and $R^6$ are independently hydrogen, a $C_1$-$C_{18}$ alkyl group or a $C_6$-$C_{18}$ aryl group;

m is 0 or 1; and

HX is selected from a haloid acid, a sulfuric acid or a phosphoric acid.

6. The method of claim 1, wherein compound 24 or compound 24' is reacted with M'SCN in the presence of an acid; a molar ratio of compound 24 or compound 24' to M'SCN is 1:1-5; and a reaction temperature is 50-80° C.

7. The method of claim 5, wherein compound 24 or compound 24' is reacted with M'SCN in the presence of an acid; a molar ratio of compound 24 or compound 24' to M'SCN is 1:1-5; and a reaction temperature is 50-80° C.

8. The method of claim 6, wherein the acid is an organic acid; and a molar ratio of the acid to compound 24 or compound 24' is 0.01-100:1.

9. The method of claim 7, wherein the acid is an organic acid; and a molar ratio of the acid to compound 24 or compound 24' is 0.01-100:1.

10. The method of claim 8, wherein the organic acid is selected from a formic acid, an acetic acid, a trifluoroacetic acid, a methanesulfonic acid and a p-toluenesulfonic acid or mixture thereof.

11. The method of claim 9, wherein the organic acid is selected from a formic acid, an acetic acid, a trifluoroacetic acid, a methanesulfonic acid and a p-toluenesulfonic acid or mixture thereof.

12. A compound 24 shown as the following formula:

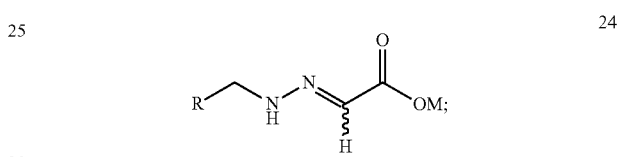

wherein:
R is selected from

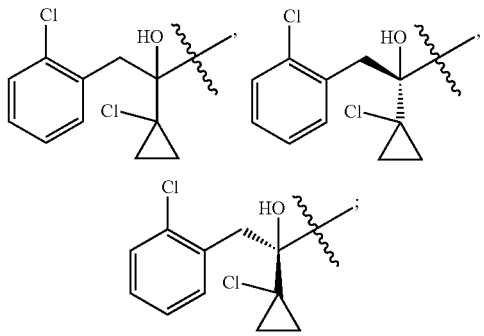

and

M is selected from hydrogen, an alkali metal or a NR³R⁴R⁵R⁶ group where $R^3$, $R^4$, $R^5$ and $R^6$ are independently hydrogen, a $C_1$-$C_{18}$ alkyl group or a $C_6$-$C_{18}$ aryl group.

13. A compound 24' shown as the following formula:

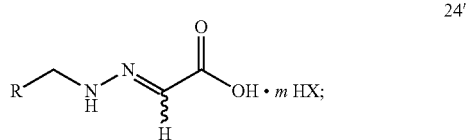

wherein:
R is selected from
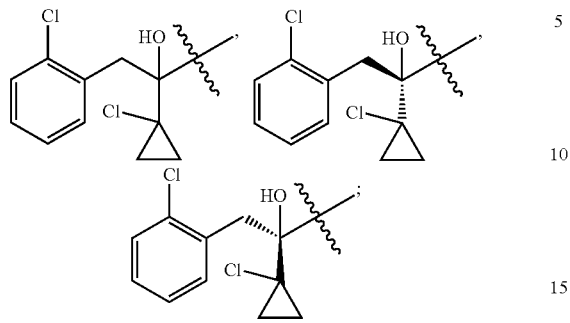
m is 0 or 1; and
HX is selected from a haloid acid, a sulfuric acid or a phosphoric acid.
* * * * *